United States Patent [19]

Scartazzini

[11] 4,411,897
[45] Oct. 25, 1983

[54] CRYSTALLINE SALTS

[75] Inventor: Riccardo Scartazzini, Basel, Switzerland

[73] Assignee: Ciba-Geigy Corporation, Ardsley, N.Y.

[21] Appl. No.: 225,295

[22] Filed: Jan. 15, 1981

[30] Foreign Application Priority Data

Feb. 1, 1980 [CH] Switzerland ............................ 836/80

[51] Int. Cl.³ .................. A61K 31/545; C07D 501/20
[52] U.S. Cl. ........................................ 424/246; 544/22
[58] Field of Search ........................... 544/22; 424/246

[56] References Cited

U.S. PATENT DOCUMENTS 4,254,119 3/1981 Hamashima et al. ................. 544/22
4,298,607 11/1981 Natsugari et al. .................... 544/27
4,316,018 2/1982 Yoshimura et al. .................. 544/27

FOREIGN PATENT DOCUMENTS 8343 3/1980 European Pat. Off. .
2810922 9/1978 Fed. Rep. of Germany .
2025933 1/1980 United Kingdom .

Primary Examiner—Paul M. Coughlan, Jr.
Attorney, Agent, or Firm—Joseph G. Kolodny

[57] ABSTRACT

The invention relates to the novel crystalline hydrochloride and the crystalline hydrobromide of 7β-[2-(2-amino-4-thiazolyl)-2-methoxyiminoacetamido]-3-cephem-4-carboxylic acid pivaloyloxymethyl ester, a process for the production thereof, and pharmaceutical preparations that contain these compounds.

6 Claims, No Drawings

CRYSTALLINE SALTS

The invention relates to novel salts in syn-form, especially the crystalline hydrochloride and the crystalline hydrobromide of 7β-[2-(2-amino-4-thiazolyl)-2-methoxyiminoacetamido]-3-cephem-4-carboxylic acid pivaloyloxymethyl ester, a process for the production thereof, and pharmaceutical preparations that contain these compounds.

7β-[2-(2-amino-4-thiazolyl)-2-methoxyiminoacetamido]-3-cephem-4-carboxylic acid pivaloyloxymethyl ester is known, for example, from European Patent Application No. 79102273.4. This compound and the salts thereof, especially those mentioned above, are valuable antibiotically active substance which can be used especially as antibacterial antibiotics.

The pivaloyloxymethyl ester, both in the form of the free base and in the form of the hydrochloride or hydrobromide, has the advantage over the similarly known sodium salt of 7β-[2-(2-amino-4-thiazolyl)-2-methoxyiminoacetamido]-3-cephem-4-carboxylic acid that, in laboratory animals, for example rats, it is absorbed from the gastrointestinal tract after oral administration to a significantly better degree and, for this reason, is more effective in the case of oral administration in chemotherapeutic tests. For example, when administered orally twice to mice, the pivaloyloxymethyl ester in the form of the free base has an $ED_{50}$ of approximately 0.7 to 30 mg/kg against gram-positive cocci, such as *Staphylococcus aureus* 10B and *Streptococcus pyogenes Aronson*, an $ED_{50}$ of approximately <0.1 to 12 mg/kg against enterobacteria, for example *Escherichia coli* 205, *Escherichia coli* 2018, *Escherichia coli* 205 R+$_{TEM}$, *Klebsiella pneumoniae* 327, *Proteus mirabilis* 774, *Salmonella Stanley* and *Proteus morganii* 2359, and an $ED_{50}$ of <100 mg/kg against Pseudomonas sp., such as *Pseudomonas aeruginosa*. As compared with the free base, the novel salts of the ester are absorbed more completely and accordingly exhibit greater chemotherapeutic effectiveness in some cases, for example the hydrochloride against *Streptococcus pyogenes Aronson*, *Escherichia coli* 205 and 218, *Klebsiella pneumonia* 327, *Proteus morganii* 2359 and *Pseudomonas aeruginosa* ATCC 12055.

One of the disadvantages of the pivaloyloxymethyl ester is that it is difficult to purify. It has not yet been possible to obtain it in crystalline form. Owing to its amorphous and impure character, it has a low degree of stability which has adverse effects during storage and when pressing tablets. Furthermore, its relatively low pourability causes problems when processing it to form tablets and when placing it in ampoules. The sparing water-solubility of the ester results in non-uniform absorption after oral administration.

The pivaloyloxymethyl ester known hitherto only in the form of the free base therefore has certain properties that are undesirable for a medicament because they render more difficult the preparation and the use of pharmaceutical forms of administration prepared therefrom. There was, therefore, a need for derivatives that are more suitable for the purposes mentioned.

In the search for suitable derivatives, surprisingly, the hydrochloride and the hydrobromide of 7β-[2-(2-amino-4-thiazolyl)-2-methoxyiminoacetamido]-3-cephem-4-carboxylic acid pivaloyloxymethyl ester in crystalline form were found which possess to a substantially greater degree the properties required of a medicament.

Owing to the capacity of these salts to crystallise, they can be purified far more easily and to a greater extent than the free base. Other advantages are their increased stability and storage capability, and improved processing characteristics in the production of pharmaceutical administration forms. In particular, they can be dried more easily and, owing to their increased stability at elevated temperatures and pressures, can be pressed better into tablets. Their greater pourability makes the filling of capsules and phials easier. The increased water-solubility results in a more uniform distribution and a more complete absorption in the gastro-intestinal tract. Consequently, great advantages are obtained, especially in the case of oral administration, as compared with the free base.

The salts according to the invention are produced in a manner known per se. The process for the production of crystalline 7β-[2-(2-amino-4-thiazolyl)-2-methoxyiminoacetamido]-3-cephem-4-carboxylic acid pivaloyloxymethyl ester hydrochloride or hydrobromide is characterised in that 7β-[2-(2-amino-4-thiazolyl)-2-methoxyiminoacetamido]-3-cephem-4-carboxylic acid pivaloyloxymethyl ester is converted by treatment with hydrogen chloride or hydrogen bromide into the hydrochloride or hydrobromide and the resulting salt is caused to crystallise.

The free base can be used in crude or purified form. The hydrogen chloride or hydrogen bromide is used in aqueous form or, preferably, in anhydrous form, and preferably in an approximately equivalent amount, i.e. depending on the purity of the base used, from approximately 0.8 to 1.2, preferably from 1 to 1.1, mol equivalents of hydrogen chloride or hydrogen bromide are used. The salt formation is advantageously carried out in a solvent, such as water, an organic solvent or mixtures thereof. The organic solvents used for the bases may be, for example, alcohols, such as methanol, ethanol, n-propanol, isopropanol, butanol or isobutanol; ketones, for example acetone or methyl ethyl ketone; nitriles, for example acetonitrile; ethers, for example tetrahydrofuran, dioxan, diethyl ether or higher ethers; sulphoxides, for example dimethyl sulphoxide; amides, for example formamide, N,N-dimethylformamide or N,N-dimethylacetamide; esters, for example ethyl acetate or methylcellosolve; or halogenated hydrocarbons, for example methylene chloride, chloroform or the like. The hydrogen chloride or hydrogen bromide also is best dissolved in one of these solvents and added to a solution of the amine. The hydrogen chloride can alternatively be introduced into the solution of the amine is gaseous form. The hydrogen chloride or hydrogen bromide solution can be used in saturated form or in unsaturated to dilute form. Preferably, the base is dissolved in methylene chloride and the calculated amount of a solution of hydrogen chloride or hydrogen bromide in an organic solvent, preferably also methylene chloride or, alternatively, methylene bromide or diethyl ether, is added thereto.

After the addition of the hydrogen chloride or hydrogen bromide, the solution containing the salt is concentrated by evaporating the solvent and/or a non-polar solvent, for example diethyl ether or a hydrocarbon, such as pentane or hexane, is added thereto, whereupon, after exceeding the solubility product, the hydrochloride or hydrobromide precipitates. Depending on the degree of purity of the starting material used, the salts precipitate in an amorphous form or already in crystalline form. Precipitation can be completed by cooling the precipitation solution.

The salt formation is carried out at a temperature of between approximately −10° and +40° C., preferably between approximately 0° and 30° C. High temperatures and an excess of hydrogen chloride or hydrogen bromide should be avoided since these can cause decomposition to occur. The precipitated salt is isolated by customary separating methods, for example by filtration or centrifugation, and washed with a non-polar solvent in which the crystals are insoluble or sparingly soluble. If the quality of the precipitate is still unsatisfactory with regard to purity and crystalline form, it can be improved by dissolving the precipitate in one or more of the mentioned solvents and then allowing crystallisation. Preferably, the first precipitate of the salt is purified by recrystallisation from methylene chloride. Whereas the amorphous salts, especially at room temperature or while heating slightly, are readily soluble in methylene chloride, the crystalline forms are virtually insoluble. They form on leaving the mixture to stand, expecially at low temperatures, for example at 0°-5° C. If necessary, the recrystallisation process is repeated until a salt is obtained that is pure according to analysis.

The preparation is advantageously dried in a high vacuum at approximately room temperature to approximately 30° C., optionally in the presence of one of the customary drying agents.

It is known that 2-aminothiazole compounds of the present kind may be present in their tautomeric 2-iminothiazoline form. According to MNR spectroscopy, the hydrochloride according to the invention is in the 2-ammoniothiazole form in DMSO.d6. In a different solvent, however, the 2-iminiothiazoline form could also be formed.

The crystalline salts of the present invention can be used for the production of pharmaceutical preparations that contain an effective amount of the active substance optionally in admixture with inorganic or organic, solid or liquid, pharmaceutically acceptable carriers that are suitable especially for oral administration. For oral administration, tablets, dry-filled capsules or gelatin capsules are used that contain the active substance together with diluents, for example lactose, dextrose, sucrose, mannitol, sorbitol, cellulose and/or glycine, and lubricants, for example silica, talc, stearic acid or salts thereof, such as magnesium or calcium stearate, and/or polyethylene glycol. Tablets also contain binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrating agents, for example starches, agar, alginic acid or salts thereof, such as sodium alginate, and/or effervescing mixtures, or absorbents, colouring substances, flavourings and sweeteners. Suppositories are, especially, fatty emulsions or suspensions.

The pharmaceutical preparations can be sterilised and/or contain adjuncts, for example preservatives, stabilisers, wetting agents and/or emulsifiers, solubilisers, and/or buffers. The present pharmaceutical preparations, which may, if desired, contain other pharmacologically valuable substances, are produced in a manner known per se, for example by means of conventional mixing, dissolving or lyophilising processes, and contain from approximately 0.1% to 100%, especially from approximately 1% to approximately 50%, and in the case of lyophilisates up to 100%, of the active substance. Depending on the type and severity of the infection and the condition of the infected organism, daily doses of from approximately 0.5 g to approximately 5 g p.o. are used for the treatment of warm-blooded animals weighing approximately 70 kg.

The following Examples serve to illustrate the invention; temperatures are given in degrees Centigrade. $R_f$ data for thin-layer chromatography: TLC: on ready-made silica gel plates SL 254 manufactured by Antec, Birsfelden.

EXAMPLE 1

61 ml of a 0.18 M HCl solution in $CH_2Cl_2$ (1.1 mol equivalent, prepared by introducing dry gaseous hydrogen chloride into dry $CH_2Cl_2$) are added to a solution, cooled to 0°, of 4.97 g of 7β-[2-(2-amino-4-thiazolyl)-2-methoxyiminoacetamido]-3-cephem-4-carboxylic acid pivaloyloxymethyl ester (free base) in 50 ml of $CH_2Cl_2$. After stirring for 10 minutes, diethyl ether is added to the solution and a precipitate forms. The mixture is stirred for a further ½ hour at 0°, the precipitate is filtered off, washed with diethyl ether and dried in a high vacuum at 30°. The crude hydrochloride is obtained as a pale beige powder which is dissolved in approximately 50 ml of $CH_2Cl_2$, concentrated slightly and left to stand overnight at approximately 5°. The compound that has crystallised out is filtered off, washed with a little $CH_2Cl_2$ and diethyl ether and dried as described above. The colourless 7β-[2-(2-amino-4-thiazolyl)-2-methoxyiminoacetamido]-3-cephem-4-carboxylic acid pivaloyloxymethyl ester hydrochloride having a melting point of 187°-191° is obtained in syn-form.

$[\alpha]_D^{20} = +82 \pm 1°$ (c = 0.689% in methanol);

TLC: $R_f \sim 0.29$ (silica gel; ethyl acetate);

UV spectrum (EtOH): maxima at 235 (ε = 16600), 245(sh) and 296(sh) mμ;

IR spectrum (Nujol): absorption bands at 3240, 1778, 1757, 1750, 1738, 1658, 1626, 1590, 1665 $cm^{-1}$;

NMR spectrum (DMSO.d6): 100 MHz. δ = 1.18 s, 9H (—C(CH$_3$)$_3$), δ = 3.70 m, 2H (H-2), δ = 3.98 s, 3H (OCH$_3$), δ = 5.19 2H, d, J = 4.5 (H-6), δ = 5.96 m, 3H (H-7 and —OCH$_2$O—), δ = 6.63 t, 1H (H-3), δ = 6.97 s, 1H (thiazole-H), δ = 9.56 b, 3H (—NH$_3^\oplus$), δ = 9.83 d, 1H, J = 8 (CONH).

Microanalysis: found: C 42.79%, H 4.44%, N 13.30%, S 11.71%, Cl 6.51%; calculated: 42.74%, 4.53%, 13.12%, 12.01%, 6.64%.

X-ray powder analysis: The sample is crystalline.

EXAMPLE 2

2.72 ml of a 0.46 M HBr solution in $CH_2Cl_2$ (≙ 1.25 mol equivalents) are added, while stirring, to a solution, cooled with ice, of 497 mg of 7β-[2-(2-amino-4-thiazolyl)-2-methoxyiminoacetamido]-3-cephem-4-carboxylic acid pivaloyloxymethyl ester (free base) in 5 ml of $CH_2Cl_2$. After stirring for 10 minutes, 35 ml of diethyl ether are added to the solution and a precipitate forms. The mixture is stirred for a further ½ hour at 0°, the precipitate is filtered off, washed with diethyl ether and dried on a suction filter. The resulting faintly orange powder is dissolved in 2.5 ml of $CH_2Cl_2$, whereupon the product recrystallises. After the addition of 5 ml of $CH_2Cl_2$, the mixture is stirred for one hour while cooling with ice. Filtration, washing of the resulting crystals with $CH_2Cl_2$ and diethyl ether and drying in a high vacuum yield the 7β-[2-(2-amino-4-thiazolyl)-2-methoxyiminoacetamido]-3-cephem-4-carboxylic acid pivaloyloxymethyl ester hydrobromide in syn-form having a melting point of 215° (with decomposition).

TLC: $R_f \sim 0.31$ (silica gel; ethyl acetate);

UV spectrum (EtOH): maxima at 225 ($\epsilon = 17520$), 231 ($\epsilon = 16920$), 237 ($\epsilon = 16240$), 243 ($\epsilon = 15600$) and 249 ($\epsilon = 14420$) m$\mu$;

IR spectrum (Nujol): absorption bands at 3245, 1776, 1757, 1750, 1738, 1658, 1628, 1590, 1570, 1560 cm$^{-1}$;

NMR spectrum (DMSO.d6): 100 MHz, $\delta = 1.18$ s, 9H (—C(CH$_3$)$_3$), $\delta = 3.70$ m, 2H (H-2), $\delta = 3.99$ s, 3H (OCH$_3$), $\delta = 5.20$ d, 2H; J = 5.0; (H-6), $\delta = 5.86$ m, 3H (H-7 and —O—CH$_2$—O—), $\delta = 6.65$ t, 1H (H-3), $\delta = 9.07$ b, 3H (—NH$_3^{\oplus}$), $\delta = 9.84$ d, 1H J = 8 (CONH).

EXAMPLE 3

Capsules containing 0.25 g of 7$\beta$-[2-(2-amino-4-thiazolyl)-2-methoxyiminoacetamido]-3-cephem-4-carboxylic acid pivaloyloxymethyl ester hydrochloride in syn-form are prepared as follows:

Composition (for 1000 capsules):

| | |
|---|---|
| 7$\beta$-[2-(2-amino-4-thiazolyl)-2-methoxyimino-acetamido]-3-cephem-4-carboxylic acid pivaloyloxymethyl ester hydrochloride in syn-form | 250.000 g |
| corn starch | 50.000 g |
| polyvinylpyrrolidone | 15.000 g |
| magnesium stearate | 5.000 g |
| ethanol | q.s. |

The 7$\beta$-[2-(2-amino-4-thiazolyl)-2-methoxyiminoacetamido]-3-cephem-4-carboxylic acid pivaloyloxymethyl ester hydrochloride in syn-form and the corn starch are mixed with each other and moistened with a solution of the polyvinylpyrrolidone in 50 g of ethanol. The moist mass is pressed through a sieve having a mesh width of 3 mm and dried at 45°. The dry granules are sieved through a sieve having a mesh width of 1 mm and mixed with 5 g of magnesium stearate. The mixture is placed in portions of 0.320 g in size 0 dry-filled capsules.

EXAMPLE 4

Tablets containing 250 mg of 7$\beta$-[2-(2-amino-4-thiazolyl)-2-methoxyiminoacetamido]-3-cephem-4-carboxylic acid pivaloyloxymethyl ester hydrochloride in syn-form are prepared as follows:

Composition (for 1 tablet):

| | |
|---|---|
| 7$\beta$-[2-(2-amino-4-thiazolyl)-2-methoxyimino-acetamido]-3-cephem-4-carboxylic acid pivaloyloxymethyl ester hydrochloride in syn-form | 250 mg |
| microcrystalline cellulose | 80 mg |
| sodium carboxymethyl starch | 10 mg |
| magnesium stearate | 3 mg |
| talc | 7 mg |
| | 350 mg |

The active substance is homogeneously mixed with the additives and pressed into tablets.

To produce film dragées, each tablet is coated with 1 mg of aqueous lacquer.

Sodium carboxymethylcellulose can be used instead of sodium carboxymethyl starch.

Capsules and tablets containing 7$\beta$-[2-(2-amino-4-thiazolyl)-2-methoxyiminoacetamido]-3-cephem-4-carboxylic acid pivaloyloxymethyl ester hydrobromide in syn-form as active substance are prepared in the same manner.

What is claimed is:

1. Crystalline 7$\beta$-[2-(2-amino-4-thiazolyl)-2-methoxyiminoacetamido]-3-cephem-4-carboxylic acid pivaloyloxymethyl ester hydrochloride in syn-form.

2. Crystalline 7$\beta$-[2-(2-amino-4-thiazolyl)-2-methoxyiminoacetamido]-3-cephem-4-carboxylic acid pivaloyloxymethyl ester hydrobromide in syn-form.

3. Pharmaceutical preparations containing an antibacterially effective amount of the crystalline hydrochloride in syn-form of claim 1.

4. Pharmaceutical preparations containing an antibacterially effective amount of the crystalline hydrobromide in syn-form of claim 2.

5. A method of treating an organism in need of antibacterial treatment which comprises administering to said organism an antibacterially effective amount of the crystalline hydrochloride of claim 1.

6. A method of treating an organism in need of antibacterial treatment which comprises administering to said organism an antibacterially effective amount of the crystalline hydrobromide of claim 2.

* * * * *